(12) United States Patent
Zeng et al.

(10) Patent No.: US 12,057,224 B2
(45) Date of Patent: Aug. 6, 2024

(54) ADAPTIVE CONTROL METHOD AND SYSTEM FOR UPPER LIMB REHABILITATION ROBOT BASED ON GAME THEORY AND SURFACE ELECTROMYOGRAPHY (sEMG)

(71) Applicant: SOUTHEAST UNIVERSITY, Nanjing (CN)

(72) Inventors: Hong Zeng, Nanjing (CN); Qingqing Chen, Nanjing (CN); Xiao Li, Nanjing (CN); Yinxin Duan, Nanjing (CN); Jianxi Zhang, Nanjing (CN); Aiguo Song, Nanjing (CN)

(73) Assignee: SOUTHEAST UNIVERSITY, Nanjing (CN)

( * ) Notice: Subject to any disclaimer, the term of this patent is extended or adjusted under 35 U.S.C. 154(b) by 0 days.

(21) Appl. No.: 18/031,152

(22) PCT Filed: Jul. 25, 2022

(86) PCT No.: PCT/CN2022/107558
§ 371 (c)(1),
(2) Date: Apr. 11, 2023

(87) PCT Pub. No.: WO2023/240748
PCT Pub. Date: Dec. 21, 2023

(65) Prior Publication Data
US 2024/0096483 A1  Mar. 21, 2024

(30) Foreign Application Priority Data
Jun. 14, 2022 (CN) .......................... 202210665652.1

(51) Int. Cl.
*G16H 40/63* (2018.01)
*A61H 1/02* (2006.01)
*G05B 13/02* (2006.01)

(52) U.S. Cl.
CPC ........... *G16H 40/63* (2018.01); *A61H 1/0274* (2013.01); *G05B 13/027* (2013.01);
(Continued)

(58) Field of Classification Search
CPC ........ G16H 20/00; G16H 20/30; G16H 40/00; G16H 40/40; G16H 40/60–67;
(Continued)

(56) References Cited

U.S. PATENT DOCUMENTS

2007/0282228 A1  12/2007  Einav et al.
2008/0009771 A1*  1/2008  Perry ................... A61H 1/0281
                                          600/587
2018/0307314 A1* 10/2018  Connor ................... G06F 3/017

FOREIGN PATENT DOCUMENTS

CN  101061984 A  10/2007
CN  101301250 A  11/2008
(Continued)

OTHER PUBLICATIONS

Sole' Ariza, Anna. "Simulation of interactive motor behaviours in game theory framework for upper-limb rehabilitation". Published: Jul. 31, 2019. Accessed from https://upcommons.upc.edu/handle/2117/167482. (Year: 2019).*
(Continued)

*Primary Examiner* — Valerie L Woodward
*Assistant Examiner* — Paige Kathleen Bugg
(74) *Attorney, Agent, or Firm* — Bayramoglu Law Offices (57) ABSTRACT

An adaptive control method and system for an upper limb rehabilitation robot based on a game theory and surface Electromyography (sEMG) is disclosed. A movement trajectory that a robot is controlled to run within a training time is designed during subject operation. An sEMG-based Back Propagation Neural Network (BPNN) muscle force estimation model establishes a nonlinear dynamic relationship
(Continued)

between an sEMG signal and end force by constructing a three-layer neural network. A human-computer interaction system is analyzed by the game theory principle, and a role of the robot is deduced. The control rate between the robot and a subject is updated by Nash equilibrium, and adaptive weight factors of the robot and the subject are determined. The robot adaptively adjusts the training mode thereof according to a movement intention of the subject during operation and a weight coefficient obtained by the game theory principle.

4 Claims, 5 Drawing Sheets

(52) U.S. Cl.
CPC ............ *A61H 2201/1659* (2013.01); *A61H 2201/5007* (2013.01); *A61H 2230/605* (2013.01)

(58) Field of Classification Search
CPC .......... A61H 1/00–0266; A61H 1/0292–0296; G05B 13/027; B25J 9/0006; A63B 21/00–4049; A63B 23/00–20; A63B 23/14–16; A63B 71/0616; A63B 71/0622; A63B 2071/0619; A63B 2071/0655; A63B 2071/0636; A63B 2024/0096
USPC .......................................................... 601/5
See application file for complete search history.

(56) References Cited

FOREIGN PATENT DOCUMENTS

| | | | |
|---|---|---|---|
| CN | 108187310 A | | 6/2018 |
| CN | 109394476 A | | 3/2019 |
| CN | 109475460 A | | 3/2019 |
| CN | 110856685 A | * | 3/2020 |
| CN | 111696645 A | * | 9/2020 |
| CN | 113081671 A | * | 7/2021 | ............ A61H 1/0274
| CN | 113633521 A | * | 11/2021 |
| CN | 114159080 A | * | 3/2022 |
| JP | 2019025104 A | | 2/2019 |
| WO | WO-2021046209 A1 | * | 3/2021 | ............ A41D 13/005

OTHER PUBLICATIONS

Qle, Xiaohan, Kang, Cunfeng, Zong, Guanchen, and Chen, Shujun. "Trajectory Planning and Simulation Study of Redundant Robotic Arm for Upper Limb Rehabilitation Based on Back Propagation Neural Network and Genetic Algorithm" Published: May 27, 2022. Accessed from https://www.mdpi.com/1424-8220/22/11/4071 (Year: 2022).*
Wang, Qi, and Wang, Xianping. "Deep Convolutional Neural Network for Decoding EMG for Human Computer Interaction". Published: Dec. 25, 2020. Accessed from https://ieeexplore.ieee.org/abstract/document/9298064 (Year: 2020).*
Translation of CN-113633521-A. Accessed from Espacenet on Jan. 17, 2023. (Year: 2021).*
Translation of CN-114159080-A. Accessed from Espacenet Jan. 17, 2023. (Year: 2022).*
Translation of CN-111696645-A. Accessed from Espacenet Jan. 17, 2023. (Year: 2020).*
Translation of CN-110856685-A. (Year: 2020).*
D. Bai et al., "Intelligent prosthetic arm force control based on sEMG analysis and BPNN classifier," 2017 IEEE International Conference on Cyborg and Bionic Systems (CBS), Beijing, China, 2017, pp. 108-113, doi: 10.1109/CBS.2017.8266078. (Year: 2017).*
Translation of CN 113081671 (Year: 2021).*
Kai Liu, Design Method of Exoskeleton Robot Based on the Coordination Movement Characteristics of Human Upper Limb, A Dissertation Submitted in Partial Fulfillment of the Requirements for the Degree of Doctor of Philosophy in Engineering, 2018, pp. 1-120.
Jiang Han, et al., Deterministic Adaptive Robust Control With a Novel Optimal Gain Design Approach for a Fuzzy 2-DOF Lower Limb Exoskeleton Robot System, IEEE Transactions on Fuzzy Systems, 2021, pp. 2373-2387, vol. 29, No. 8.

* cited by examiner

ADAPTIVE CONTROL METHOD AND SYSTEM FOR UPPER LIMB REHABILITATION ROBOT BASED ON GAME THEORY AND SURFACE ELECTROMYOGRAPHY (sEMG)

CROSS-REFERENCES TO THE RELATED APPLICATIONS

This application is the national stage entry of International Application No. PCT/CN2022/107558, filed on Jul. 25, 2022, which is based upon and claims priority to Chinese Patent Application No. 202210665652.1 filed on Jun. 14, 2022, the entire contents of which are incorporated herein by reference.

TECHNICAL FIELD

The present invention belongs to the technical field of machine learning, and in particular to the technical field of rehabilitation robots and machine learning of rehabilitation training, and mainly relates to an adaptive control method and system for an upper limb rehabilitation robot based on a game theory and surface Electromyography (sEMG).

BACKGROUND

According to the World Health Organization (WHO) and the existing official demographic data, the problem of aging in the world is becoming more and more serious, leading to a continuous increase in the incidence of age-related diseases, such as stroke and Parkinson's disease. Stroke is also called cerebral stroke. In China, there are more than 2 million new cerebral stroke patients every year, and more than 1.5 million people die of cerebral stroke every year. With the influence of lifestyle and other external factors, the incidence and mortality of cerebral stroke are on the rise in recent years. Due to the irreversibility of brain injury, the missing function cannot be completely recovered, and motor dysfunction is the most common sequelae. Upper limbs play an important role in body movement, posture maintenance, balance, etc. The decline or lack of the functions of the upper limbs not only seriously affects the quality of life of a patient, but also brings pain and heavy economic burden to the patient and his family. Many stroke patients will experience long-term sports disability and need labor-intensive exercise therapy as soon as possible and for a long time, which brings a heavy burden to the medical system.

With the rapid development of artificial intelligence, the robot technology has been gradually applied in the field of rehabilitation medicine. Rehabilitation robots with virtual reality, intelligent force feedback, intelligent evaluation and other technologies have been developed at home and abroad. Such devices may increase sensory input through a computer screen, an interactive virtual reality device and a tactile sensing system. The computer system shows a virtual scene and a guiding task to the patient, and the patient carries out resistance, non-resistance and other exercise training through a mechanical part attached to the limbs, thus restoring his motor functions. The main advantages of the technologies are that the patient can be provided with high dose, high intensity, high repeatability and targeted training, and the training mode is more interesting than traditional rehabilitation training, which may mobilize the enthusiasm of the patient for training. A sensor may record information such as the movement trajectory and the movement time of the patient and make intelligent evaluation and analysis. A therapist or doctor may adjust the treatment plan in time through the information, which is conducive to speeding up the patient's rehabilitation process.

A rehabilitation training mode is one of the important research contents of a rehabilitation robot system, which is divided into a passive mode and an active mode, and is suitable for different rehabilitation stages of the patient, respectively. Passive rehabilitation training refers to the mode that a rehabilitation robot drives the human arm to carry out rehabilitation training. Active training refers to the training mode in which the human arm exerts force and the rehabilitation robot provides assistance or resistance. Research shows that even if the patient does not have the ability to complete exercise, the willingness to actively exercise is necessary for rehabilitation training. Therefore, human-computer interaction control is extremely important in rehabilitation training. The desired control solution is to identify the movement intention of a human body by estimating the joint torque of the human body so as to adaptively select the robot training mode. A human skin sEMG signal is a biologically generated signal, which can accurately and quickly reflect the movement intention of a user. The EMG signal generated by muscle contraction is 20~150 ms earlier than the joint torque, and has a shorter time delay and higher signal-to-noise ratio than a force sensor. The sEMG signal may be an ideal source for estimating the active joint torque. However, in the existing robot-assisted therapy, the force is measured mostly based on the force sensor, and the sEMG signal is scarcely used to estimate the force during the movement. On the other hand, with the progress of the patient' rehabilitation, resistance training is very important for strengthening muscles. Therefore, during rehabilitation training of the patient, adaptive mode switching and flexible control over end force output are very important. At present, most of the human-computer interaction control methods are not flexible enough for a cooperative task, and generally auxiliary training or resistance training can only be performed alone, or hard switching between multiple controllers is performed, which may lead to discontinuous overall control input, and further lead to a violent jitter of the robot during mode switching and even endanger human safety.

SUMMARY

Aiming at the problem existing in a multi-mode switching process of a robot in a prior art, the present invention provides an adaptive control method for an upper limb rehabilitation robot based on a game theory and sEMG. First, a trajectory following task is designed, and a movement trajectory that a robot is controlled to run within a training time is designed during subject operation. Then a muscle force estimation model of an sEMG-based Back Propagation Neural Network (BPNN) is designed, and a nonlinear dynamic relationship between an sEMG signal and end force is established by constructing a three-layer neural network. A human-computer interaction system is analyzed by a game theory principle, and a role of the robot is deduced. The control rate between the robot and a subject is updated by Nash equilibrium, and adaptive weight factors of the robot and the subject are determined. When the weight factor Q of the robot is positive, the robot provides auxiliary force; and when the weight factor Q of the robot is negative, the robot provides resistance force. Finally, the robot adaptively adjusts the training mode thereof according to a movement intention of the subject during operation and a weight coefficient obtained by the game theory principle, and the training mode of the rehabilitation robot can adapt to the movement intention of the upper limbs of a human body. The control method in the solution can adaptively change the working mode of the rehabilitation robot according to the movement intention of the human body, and can fully consider a change of the training process of the subject to provide a corresponding training task in real time, thus ensuring the participation of the subject during training, effectively stimulating the nerves to cause neural function reorganization, and improving the training efficiency of the rehabilitation robot.

In order to achieve the above objective, the present invention provides the following technical solution:

An adaptive control method for an upper limb rehabilitation robot based on a game theory and surface Electromyography (sEMG), comprising the following steps:

S1, designing a trajectory following task: the trajectory following task is to control the robot to move within a training time during subject operation, and the task at least comprises a reference trajectory for the movement of a subject and the training time;

S2, identifying a movement intention of the subject: designing a muscle force estimation model of an sEMG-based Back Propagation Neural Network (BPNN), and establishing a nonlinear dynamic relationship between an sEMG signal and end force by constructing a three-layer neural network, wherein the BPNN-based muscle force estimation model is divided into three layers, which are an input layer, a hidden layer and an output layer, respectively, input data is a smoothed sEMG signal after filtering and normalization (RSEMG), and the output is estimated force F;

S3, adaptive switching of a training mode: analyzing a human-computer interaction system by the game theory principle, deducing a role of the robot, updating the control rate between the robot and the subject by Nash equilibrium, and determining adaptive weight factors of the robot and the subject, $$Q + Q_h = C$$

where Q is the weight factor of the robot, $Q_h$ is the weight factor of the subject, and C is a constant;

when the weight factor Q of the robot is positive, the robot provides auxiliary force;

when the weight factor Q of the robot is negative, the robot provides resistance force; and S4, an adaptive control strategy: during training, the robot adaptively adjusts the training mode thereof according to the movement intention of the subject during the operation and a weight coefficient obtained according to the game theory principle.

In order to achieve the above objective, the present invention provides the following technical solution:

An adaptive control system for an upper limb rehabilitation robot based on a game theory and surface Electromyography (sEMG), comprising a trajectory designing module, a movement intention identification module and an adaptive control module, wherein the trajectory designing module is configured to design a trajectory following task, that is, to control a movement trajectory design of the robot within a training time during subject operation;

the movement intention identification module is configured to design a muscle force estimation model of an sEMG-based Back Propagation Neural Network (BPNN), and establish a nonlinear dynamic relationship between an sEMG signal and end force by constructing a three-layer neural network;

the adaptive control module analyzes a human-computer interaction system using the game theory principle according to information obtained by the trajectory designing module and the movement intention identification module, deduces a role of the robot, updates the control rate between the robot and a subject using Nash equilibrium, and determines an adaptive weight factor between the robot and the subject; when the weight factor of the robot is positive, the robot provides auxiliary force; when the weight factor of the robot is negative, the robot provides resistance force; and when the weight factor of the robot is zero, the robot does not provide force, which is a free training mode.

Compared with the prior art, the present invention has the beneficial effects that:

(1) This method is based on the sEMG signal, uses the BPNN to establish a force estimation model and predict the human movement intention, and can provide the best training mode adaptively according to the human movement intention during rehabilitation training, and provide the best training intensity according to the degree of human rehabilitation during training, so as to keep the subject actively training and maximize the training efficiency.

(2) The adaptive mode switching is performed using the game theory control principle. The method is stable in switching, does not produce violent jitter, and can provide a training mode that adapts to the human movement intention, stimulate the subject's neural perception of force and movement control, always keep in the best training state, and avoid useless training process as much as possible. The control strategy ensures the stability and real-time performance of adaptive switching, and provides a solution for intelligent and efficient neural rehabilitation.

DETAILED DESCRIPTION OF THE EMBODIMENTS

The present invention is further illustrated below in conjunction with the drawings and specific embodiments, and it should be understood that the following specific embodiments are merely used to illustrate the present invention and not to limit the scope of the present invention.

Embodiment 1

Figure 1:
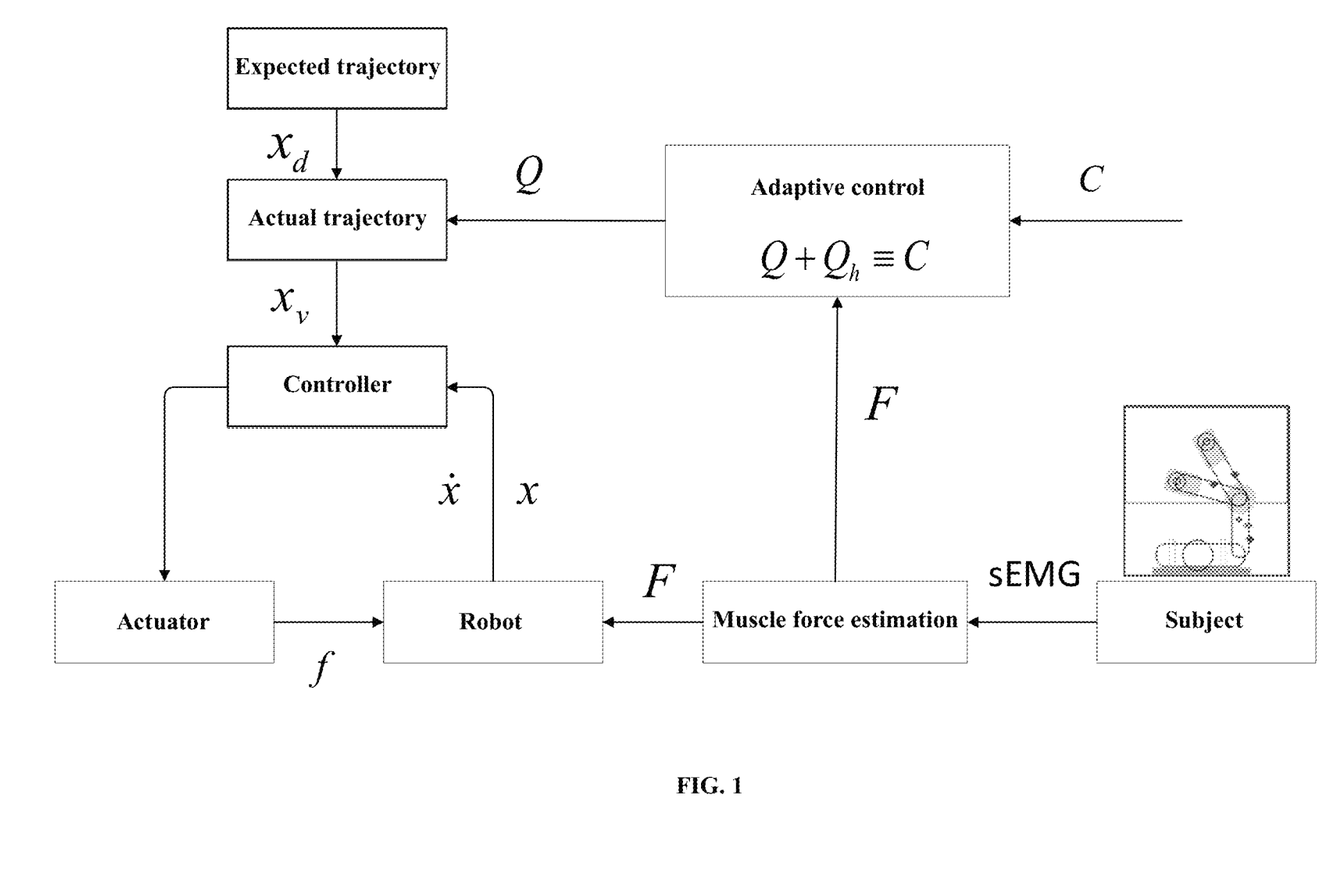
FIG. 1 is a frame diagram of overall adaptive closed-loop control of a control method of the present invention.
Figure 2:
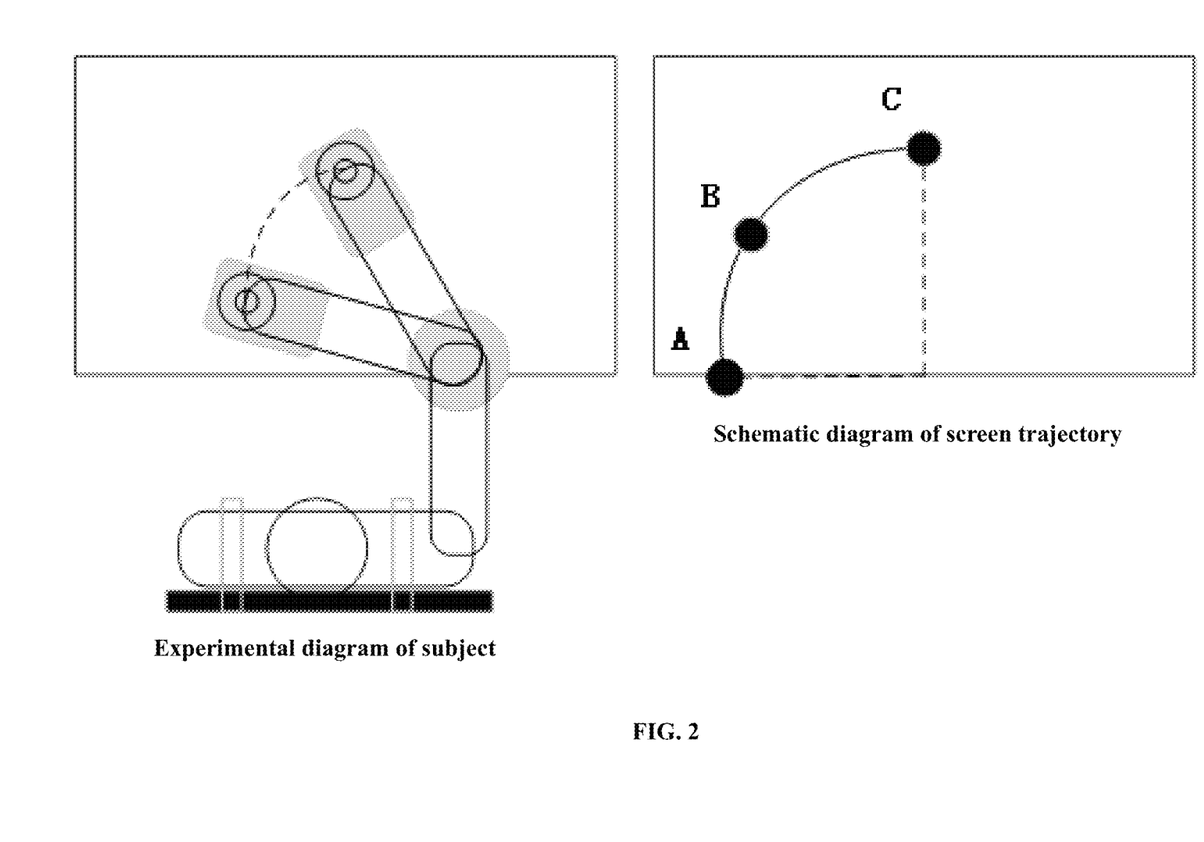
FIG. 2 is a schematic diagram of a trajectory following task designed in S1 of a control method of the present invention.

An adaptive control method for an upper limb rehabilitation robot based on a game theory and sEMG, as shown in FIG. 1, including the following steps:

S1, designing a trajectory following task: the trajectory following task is to control the robot to move within a training time during subject operation, and the task at least comprises a reference trajectory for the movement of a subject and the training time;

As shown in FIG. 2, in the embodiment, a target trajectory is designed as a quarter curve of a standard circle, and three reference points A, B and C are uniformly displayed on the trajectory as guiding points. During subject operation, an end of the robot is controlled to follow the trajectory within a specified time according to the reference points, and a subject made a cycle from a horizontal starting point to a vertical ending point and then back to the horizontal starting point in one experiment. That is, the movement trajectory is A-B-C-B-A, and each experiment is conducted for 5-8 cycles.

S2, An sEMG-based BPNN muscle force estimation model is designed:

A nonlinear dynamic relationship between an sEMG signal and end force is established by constructing a three-layer neural network. The BPNN model is divided into three layers, which are an input layer, a hidden layer and an output layer, respectively. Input data is an RSEMG signal. For the convenience of representation, RSEMG is used herein to represent the smoothed sEMG signal after filtering and normalization. Estimated force F is the output of the BPNN.

Figure 3:
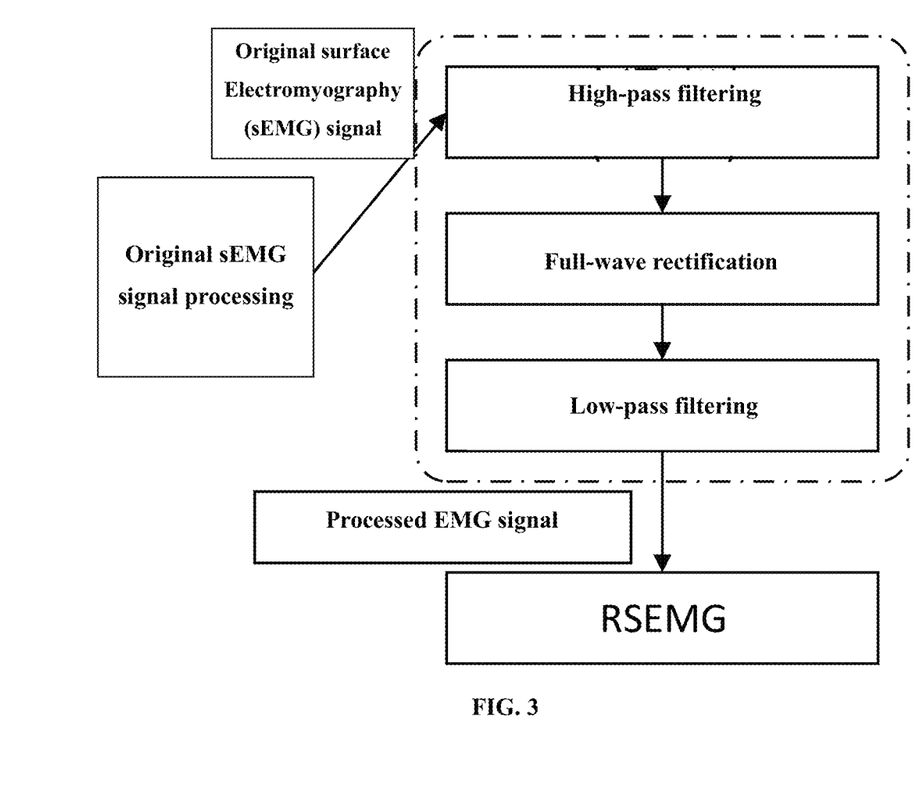
FIG. 3 is a of a RSEMG signal generated in S2 of a control method of the present invention.

During rehabilitation training, the movement state is generally monitored and characterized by the human skin sEMG signal. Since an original EMG signal may be disturbed a lot, the RSEMG signal is used, as shown in FIG. 3, that is, the original sEMG signal collected is first subjected to high-pass filtering, full-wave rectification and low-pass filtering in turn, and then normalized to obtain the RSEMG signal. The original EMG signal in the embodiment may select biceps brachii, anconeus longus, brachycephalus triceps or brachioradialis as a to-be-analyzed muscle group, as the muscle group above is mainly responsible for the motor function of the upper limbs, which is more accurate and efficient.

In addition, in view of the differences between subjects and the purpose of providing a personalized training method for each subject in the follow-up process, a three-minute pre-experiment is conducted for each subject before the experiment to collect EMG data and establish the force estimation model. The model can be trained by the data of an EMG sensor and a force sensor collected within a short time, and the modeling process may avoid the fatigue of the subject in the pre-experiment.

Figure 4:
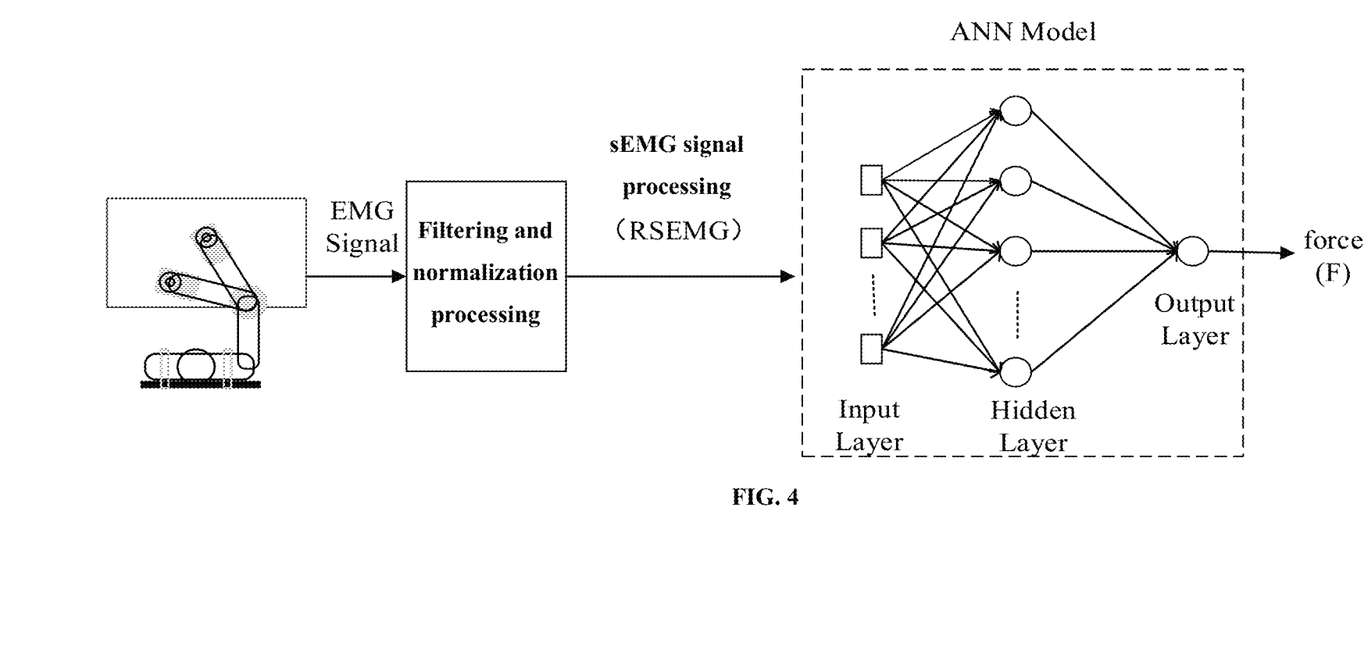
FIG. 4 is a schematic diagram of an sEMG-based force estimation model in a control method of the present invention.

In the step, the sEMG-based BPNN muscle force estimation model is shown in FIG. 4. Herein, RSEMG is used as the input of the neural network and the estimated force (F') is used as the output, and the nonlinear dynamic relationship between the sEMG signal and the end force is established by constructing the three-layer neural network.

S3, Adaptive switching of a training mode:

A human-computer interaction system is analyzed by a game theory principle, a cost function is established according to input states of the robot and the subject, the control rate between the robot and the subject is updated by Nash equilibrium, the weight of the cost function is estimated, adaptive weight factors of the robot and the subject are determined, and a role of the robot is determined according to the output weight factors.

Cost Function:

$$U = \int_{t_0}^{\infty} \xi^T(t) Q \xi(t) + u^T(t) u(t) dt$$

$$U_h = \int_{t_0}^{\infty} \xi^T(t) Q_h \xi(t) + u_h^T(t) u_h^T(t) dt$$

Nash Equilibrium:

$$u = -L\xi, L = B^T P$$

$$A_r^T P + PA_r + Q - PBB^T P = 0_{2n}, A_r = A - BL_h$$

$$u_h = -L_h \xi, L_h = B^T P_h$$

$$A_h^T P_h + P_h A_h + Q_h - P_h BB^T P_h = 0_{2n}, A_h = A - BL$$

Adaptive Weight Factor:

$$Q + Q_h = C$$

where $\xi$ represents a movement state (a trajectory error and speed), $Q Q_h$ represents weight coefficients of the robot and the subject, C is a constant, $u^{u_h}$ represents motor instructions of the robot and the subject, $L^{L_h}$ represents feedback gain of the robot and the subject, A B represents a state and an input matrix, $P P_h$ represents a Riccati matrix of the robot and the subject, $A_r$ $A_h$, represents a state matrix of the subject and the robot, and $(.)^T$ represents transposition.

S4, An adaptive control strategy:

The control strategy of the training mode is adaptively adjusted and controlled according to the human movement intention as follows: during training, first, the movement intention of the subject is estimated by an arm sEMG signal during the operation, that is, end-of-arm force is estimated.

Furthermore, according to the movement intention of the subject and the auxiliary state of the robot, the corresponding weight coefficient is obtained using the game theory principle and fed back to a motor of the robot, and then the training mode of the robot is adjusted adaptively.

When the weight of the robot is positive, the nerve intention and muscle ability of a person cannot fully guide the robot, and the robot is in the auxiliary mode. On the contrary, the movement intention of the subject is enhanced, and when the weight of the robot is zero, the robot does not provide force, which is a free training mode. When the weight of the robot is negative, resistance force is provided, which is a resistance training mode. That is, the movement intention of the human body can automatically control the working mode of the rehabilitation robot, and the adaptive rehabilitation training can be completed through the movement intention of the subject himself.

Figure 5:
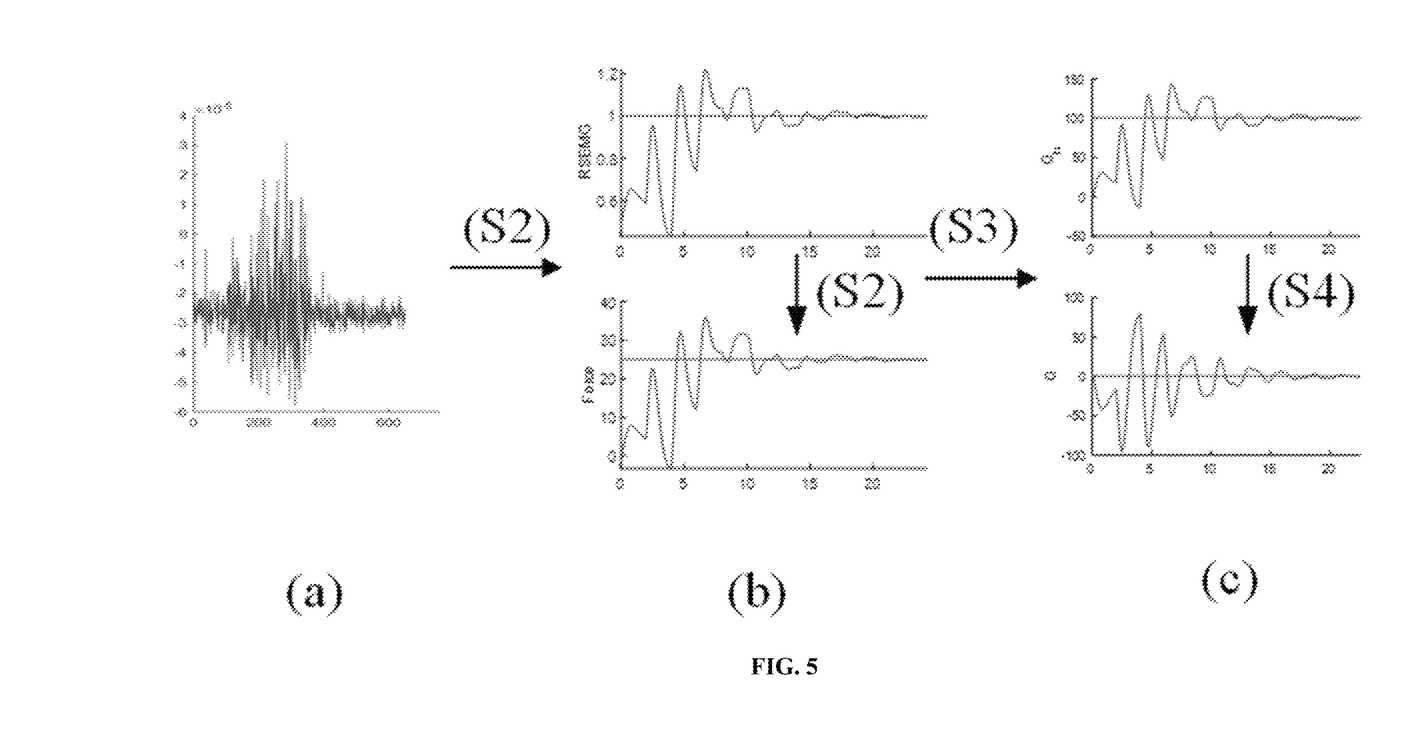
FIG. 5 is a brief example diagram of an adaptive control process of a test case of the present invention.

Test Case:

It is assumed that part of the sEMG signals collected during training of the subject shown in FIG. 5(a) is subjected to filtering and normalization shown in S2 to obtain an RSEMG signal, subjected to the muscle force estimation model described in S2 to obtain estimated muscle Force as shown in FIG. 5(b), and then subjected to the adaptive mode switching method described in S3 to obtain the roles assigned to the subject and the robot, and further to provide a corresponding auxiliary or resistance training mode. As shown in FIG. 5(c), at 0 second, the adaptive weight factor $Q_h$ value of the subject is 0, and the adaptive weight factor Q value of the robot is also 0, that is, no force is applied. In the range of 0-20s, the robot will update its own Q value adaptively according to the change of the $Q_h$ value. When the $Q_h$ value of the subject is large, that is, the movement ability is enhanced, the robot Q value will decrease, that is, the auxiliary force will be reduced or the corresponding resistance force will be provided. When the $Q_h$ value of the subject decreases, that is, the movement ability decreases, the robot Q value will increase, that is, the resistance force is decreased or the corresponding auxiliary force is provided. After 20s, when the $Q_h$ value of the subject is stable, that is, the movement ability is basically unchanged, the Q value of the robot also remains stable, and the human-computer interaction reaches a balanced state.

The control method in the solution takes a desktop force feedback robot as a carrier and research object, and takes the non-dominant arm of a healthy subject as an experimental object. The study is based on the sEMG to obtain end-of-arm force and then predict the human movement intention to realize adaptive switching of the robot training mode, which ensures that the subject provides the best auxiliary or resistance strength at any stage in the training process, is always the best personalized and intelligent training mode, ensures the participation of the subject in the training process, effectively improves the training efficiency of robot technology-assisted rehabilitation, and provides technical support for the rehabilitation robot to enter clinical applications faster.

It is to be noted that the above contents only explain the technical idea of the present invention, and cannot be used to limit the scope of protection of the present invention. For those of ordinary skill in the art, several improvements and embellishments can be made without departing from the principle of the present invention, and these improvements and embellishments shall fall within the scope of protection of the claims of the present invention.

What is claimed is:

1. An adaptive control method for an upper limb rehabilitation robot based on a game theory and surface electromyography (sEMG), comprising a series of steps including:
    step 1, which comprises designing a trajectory following task, wherein the trajectory following task comprises: uniformly assigning three reference points A, B, and C along a quarter curve of a standard circle as a trajectory, controlling the robot to follow the trajectory within a training time according to the reference points, during operation by a subject, cycling movement of the subject from a horizontal starting point to a vertical ending point and then back to the horizontal starting point, wherein a movement trajectory is A-B-C-B-A, and conducting the movement trajectory for 5-8 cycles;
    step 2, which comprises identifying a movement intention of the subject by designing a muscle force estimation model of an sEMG-based Back Propagation Neural Network (BPNN), and establishing a nonlinear dynamic relationship between an sEMG signal and an end force by constructing a three-layer neural network, wherein an original EMG signal is taken from EMG signals with biceps brachii, anconeus longus, brachycephalus triceps, or brachioradialis as a to-be-analyzed muscle group, wherein the BPNN-based muscle force estimation model is divided into three layers, including an input layer, a hidden layer and an output layer, respectively, wherein input data comprises a smoothed sEMG signal after filtering and normalization (RSEMG), and output data comprises estimated force (F) and, wherein the RSEMG signal is obtained by sequentially processing high-pass filtering, full-wave rectification, low-pass filtering, and normalization on an original sEMG signal collected 20-150 ms earlier than a torque measured from a force sensor;
    step 3, adaptive switching of a training mode by analyzing a human-computer interaction system by a game theory principle, deducing a role of the robot, updating a control rate between the robot and the subject by Nash equilibrium, and determining adaptive weight factors of the robot and the subject, $$Q+Q_h=C$$

where Q is the weight factor of the robot, $Q_h$ is the weight factor of the subject, and C is a constant;
    when the weight factor Q of the robot is positive, the robot provides auxiliary force; when the Q weight factor Q of the robot is negative, the robot provides resistance force; and
    step 4, an adaptive control strategy comprising: during training, first estimating the movement intention of the subject by an arm sEMG signal, then adaptively adjusting the training mode thereof according to the movement intention of the subject during the operation and a weight coefficient obtained according to the game theory principle which is fed back to a motor of the robot, wherein the adaptive control strategy reduces a jitter of the robot during switching.

2. The adaptive control method for the upper limb rehabilitation robot based on the game theory and the sEMG according to claim 1, wherein in step 3, in the process of analyzing the human-computer interaction system using the game theory principle, a cost function is established according to input states of the robot and the subject, and the cost function is:

$$U=\int_{t_0}^{\infty} \xi^T(t)Q\xi(t)+u^T(t)u(t)dt$$

$$U_h=\int_{t_0}^{\infty} \xi^T(t)Q_h\xi(t)+u_h^T(t)u_h^T(t)dt$$

where U and $U_h$ represent the cost functions of the robot and the subject, respectively; t represents time; $\xi$ represents a movement state; u and $u_h$ represent motor instructions of the robot and the subject, respectively; Q is the weight factor of the robot; $Q_h$ is the weight factor of the subject; $u^T$ represents transposition of u, and $u_h^T$ represents transposition of $u_h$; and $t_0$ represents start time.

3. The adaptive control method for the upper limb rehabilitation robot based on the game theory and the sEMG according to claim 2, wherein in step 3, the control rate between the robot and the subject is updated by Nash equilibrium, and the Nash equilibrium is specifically as follows:

$$u=-L\xi, L=B^TP$$

$$A_r^TP+PA_r+Q-PBB^TP=0_{2n}, A_r=A-BL_h$$

$$u_h=-L_h\xi, L_h=B^TP_h$$

$$A_h^TP_h+P_hA_h+Q_h-P_hBB^TP_h=0_{2n}, A_h=A-BL$$

where L and $L_h$ represent feedback gain of the robot and the subject, A B represents a state and an input matrix, P $P_h$ represents a Riccati matrix of the robot and the subject, $A_r$ $A_h$ represents a state matrix of the subject and the robot, and $u^T$ represents transposition of u, and $u_h^T$ represents transposition of $u_h$.

4. The adaptive control method for the upper limb rehabilitation robot based on the game theory and the sEMG according to claim 3, wherein in step 4, when the weight of the robot is zero, the robot does not provide force, which is a free training mode.

* * * * *